United States Patent
Oba

(10) Patent No.: US 6,752,797 B2
(45) Date of Patent: Jun. 22, 2004

(54) DISPOSABLE PULL-ON UNDERGARMENT

(75) Inventor: Toru Oba, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/805,595

(22) Filed: Mar. 13, 2001

(65) Prior Publication Data

US 2001/0023344 A1 Sep. 20, 2001

(30) Foreign Application Priority Data

Mar. 14, 2000 (JP) ........................................ 2000-070710

(51) Int. Cl.[7] .............................................. A61F 13/15
(52) U.S. Cl. ...................................... 604/395; 604/400
(58) Field of Search ................................ 604/393–402, 604/385.24–385.3, 385.14, 385.01; 2/78.1, 78.2, 400–408, 109, 111, 112, 80

(56) References Cited

U.S. PATENT DOCUMENTS

| | | | | |
|---|---|---|---|---|
| 3,895,629 A | * | 7/1975 | Snyder | 128/DIG. 26 |
| 4,022,212 A | * | 5/1977 | Lovison | 604/385.14 |
| 4,637,078 A | * | 1/1987 | Southwell | 2/408 |
| 4,835,795 A | * | 6/1989 | Lonon | 2/408 |
| 5,341,515 A | * | 8/1994 | Cohen | 2/400 |
| 5,708,977 A | * | 1/1998 | Morkunas | 2/80 |
| 6,243,871 B1 | * | 6/2001 | Fidler | 2/80 |
| 6,605,071 B1 | * | 8/2003 | Gray et al. | 604/385.28 |

FOREIGN PATENT DOCUMENTS

JP  9-566  1/1997

* cited by examiner

Primary Examiner—John J. Calvert
Assistant Examiner—C. Lynne Anderson
(74) Attorney, Agent, or Firm—Butzel Long

(57) ABSTRACT

A disposable pull-on undergarment including a front waist region and a rear waist region which together define a waist-opening at an upper end of the undergarment. First fastening zones are formed on the inner surface of the front waist region and extend from the vicinity of a lower end toward an upper end of the front waist region. A second fastening zone is formed on the inner surface of the rear waist region in the vicinity of its lower end. A third fastening zone is formed on the outer surface of the rear waist region and spaced apart from the second fastening zone toward the upper end. The second and third fastening zones are releasably engaged with the first fastening zones to form the undergarment with a pair of leg-openings.

8 Claims, 5 Drawing Sheets

DISPOSABLE PULL-ON UNDERGARMENT

BACKGROUND OF THE INVENTION

This invention relates to a disposable pull-on undergarment such as a diaper, training pants for infant, a diaper cover or the like.

Japanese Patent Application Publication No. 1997-566A describes a disposable pull-on diaper having front and rear waist regions each comprising a liquid-pervious topsheet, a liquid-impervious backsheet and a liquid-absorbent core disposed between the topsheet and the backsheet. These two waist regions are bonded together along respective transversely opposite side edges thereof and lower ends of these two waist regions are releasably fastened together along fastening zones to form a pair of leg-openings.

With the respective lower ends of these two waist regions disengaged from each other, the diaper is pulled upward so that the wearer's legs may pass first through a waist-opening and then through a lower opening of the diaper to the wearer's waist line in order to put the diaper on the wearer's body. The lower ends of the front and rear waist regions are adapted to be releasably fastened together along the fastening zones so that the diaper may be easily put on a wearer's body merely after the clothes such as trousers or tights already worn by the wearer has been pulled down to the wearer's knee and to protect the wearer's skin from uncomfortable stimulation which would otherwise occur.

However, with the lower ends of the front and rear waist regions being fastened together, the diaper disclosed in the Publication encounters a problem such that the lower end of the front waist region lying on the inner side of the diaper may create uncomfortable irritation against the wearer's skin.

SUMMARY OF THE INVENTION

It is an object of this invention to provide a disposable pull-on undergarment adapted to be easily put on the wearer's body merely after the clothes already worn by the wearer has been pulled down to the wearer's knee and to protect the wearer's skin from uncomfortable irritation which would otherwise occur.

According to this invention, there is provided a disposable pull-on undergarment comprising a front waist region and a rear waist region each having longitudinally opposite upper and lower ends and transversely opposite side edges, the front and rear waist regions being bonded together along sections of the side edges extending aside to the upper ends to form a waist-opening and the lower ends of the front and rear waist regions are releasably fastened together along fastening zones to form a pair of leg-openings.

The undergarment further comprises the fastening zones including a first fastening zone of a given dimension provided on an inner surface of the front waist region and extending from a vicinity of the lower end toward the upper end of the front waist region, a second fastening zone provided on the inner surface in vicinity of the lower end and releasably engaged with the first fastening zone lying adjacent the upper end of the front waist region and a third fastening zone provided on the outer surface of the rear waist region and spaced apart from the second fastening zone toward the upper end by a predetermined dimension so that the third fastening zone is engaged with the first fastening zone lying adjacent the lower end of the front waist region.

The disposable pull-on undergarment according to this invention is configured so that the respective lower ends of the front and rear waist regions may be releasably fastened together along the respective fastening zones. Therefore, the article can be easily put on the wearer's body by pulling the article upward around the wearer's thighs to the wearer's waist line so that the wearer's thighs pass first through the waist-opening and then through the lower opening of the undergarment. Such an arrangement allows the diaper 1 to be put on the wearer's body without any need for completely pulling off wearer's clothes such as trousers or tights, even if such clothes are already put on the wearer's body. In other words, the clothes may be pull down to the level of the wearer's knees immediately before putting the diaper 1 on the wearer's body.

In the undergarment according to this invention, the lower end of the rear waist region is partially folded on the outer side of the diaper as the front and rear waist regions are fastened together at the lower ends thereof so that the lower end of the rear waist region may be kept out of contact with the wearer's skin. In this way, the wearer's skin is reliably protected from uncomfortable stimulation due to the lower end which would otherwise contact the wearer's skin.

DETAILED DESCRIPTION OF THE PREFERRED EMBODIMENTS

Details of a disposable pull-on undergarment according to this invention will be more fully understood from the description given hereunder with reference to the accompanying drawings.

Figure 1:
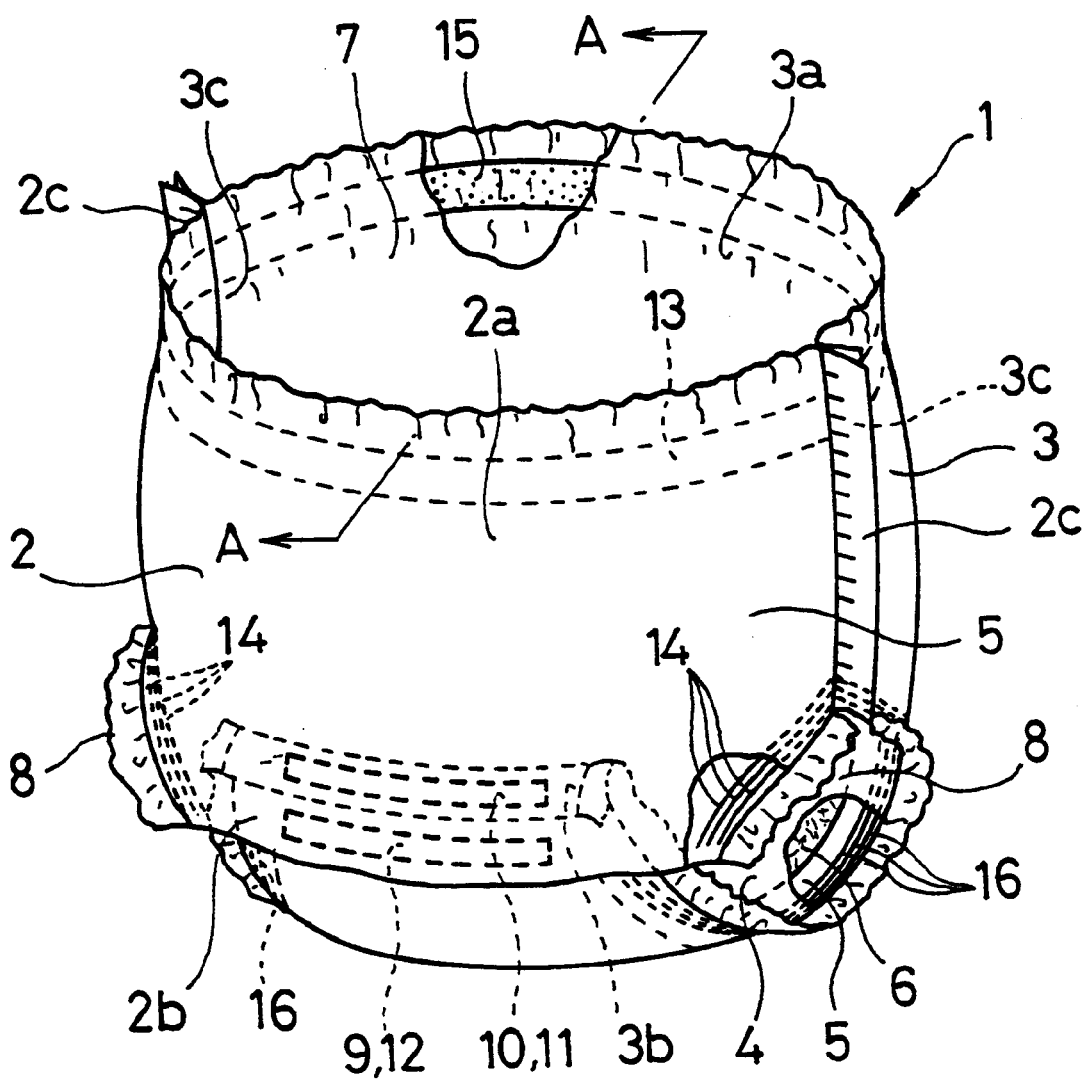
FIG. 1 is a perspective view depicting one embodiment of this invention in the form of a partially cutaway disposable diaper with its front and rear waist regions fastened together at lower ends thereof.
Figure 2:
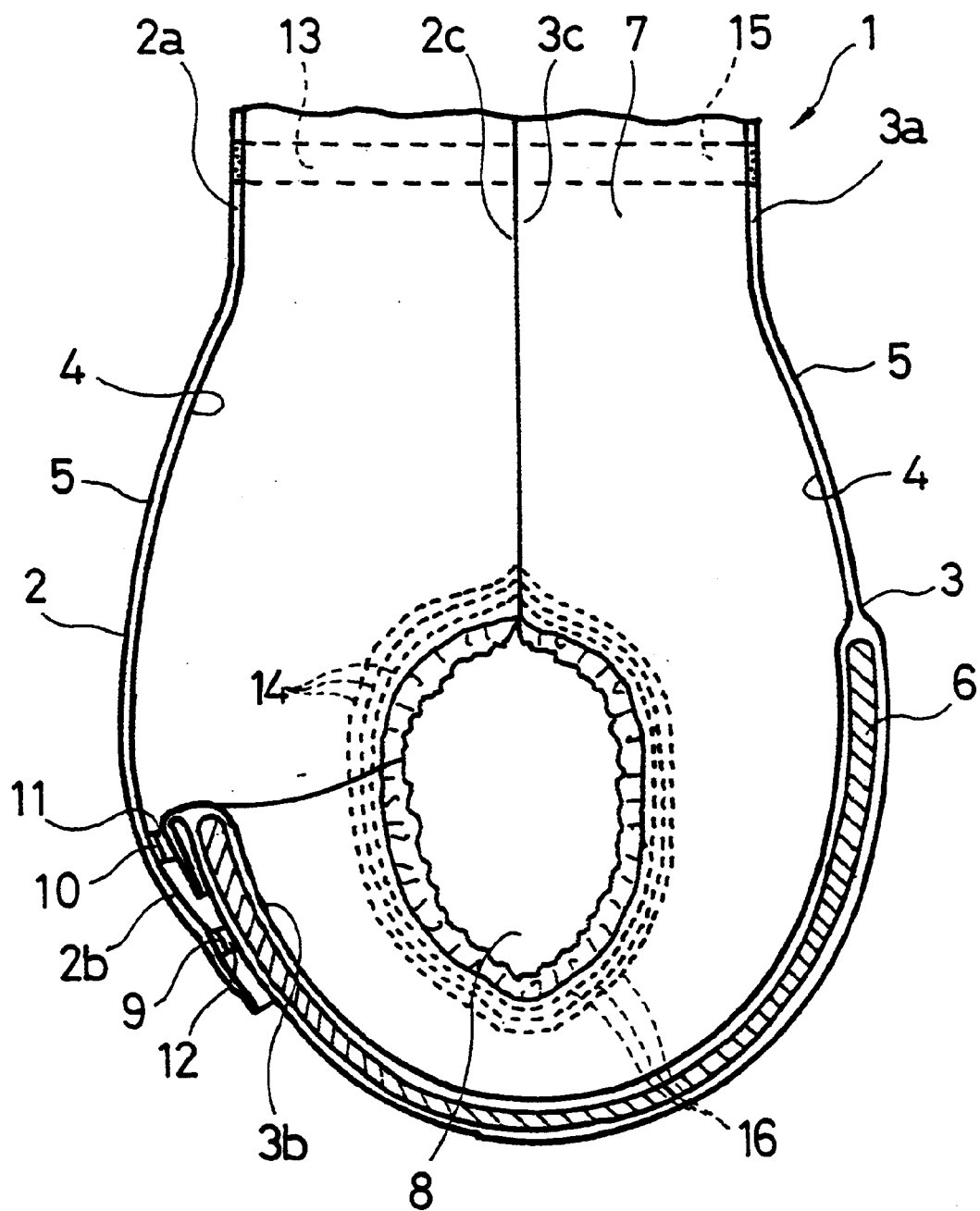
FIG. 2 is a sectional view of the diaper taken along line A—A in FIG. 1.

FIG. 1 is a perspective view depicting one embodiment of this invention in the form of a partially cutaway disposable diaper 1 with its front and rear waist regions 2, 3 fastened together at lower ends 2b, 3b thereof and FIG. 2 is a sectional view of the diaper 1 taken along line A—A in FIG. 1. The diaper 1 comprises the front waist region 2 extending on the side of wearer's belly and the rear waist region 3 extending on the side of the wearer's hip. These front and rear waist regions 2, 3 respectively have longitudinally opposite ends 2a, 2b; 3a, 3b transversely extending parallel to each other and transversely opposite side edges 2c, 2c; 3c, 3c longitudinally extending parallel to each other.

In the lower sections of the front and rear waist regions 2, 3 extending aside to the respective lower ends 2b, 3b, the respective side edges 2c, 2c; 3c, 3c extend so as to get nearer to a longitudinal center line Y bisecting a transverse dimension of the diaper 1. The waist regions 2, 3 have their lower ends 2b, 3b transversely dimensioned to be shorter than their upper ends 2a, 3a, respectively. The front waist region 2 has its longitudinal dimension between its upper and lower ends 2a, 2b smaller than a longitudinal dimension of the rear waist region 3 (See FIG. 3).

In the upper sections of the front and rear waist regions 2, 3 extending aside to the respective upper ends 2a, 3a, the respective side edges 2c, 2c; 3c, 3c are respectively put flat together and bonded to each other. On the other hand, the respective lower ends 2b, 3b of the front and rear waist regions 2, 3 are fastened together at their zones lying aside to the side of the wearer's belly by means of fastening zones 9, 10, 11, 12 formed on these waist regions 2, 3. The respective upper ends 2a, 3a of these waist regions 2, 3 define a waist-opening 7 and the sections of the respective side edges 2c, 2c; 3c, 3c extending aside to the respective lower ends 2b, 3b define a pair of leg-openings 8, 8, respectively.

The front waist region 2 comprises a liquid-pervious topsheet 4 defining its inner surface and a liquid-impervious backsheet 5 defining its outer surface. The topsheet 4 and the backsheet 5 are put flat together and bonded to each other along their peripheral edge.

The front waist region 2 is provided along its upper end 2a with a film-like elastic member 13 circumferentially extending to be associated with the waist-opening 7. This elastic member 7 is disposed between the topsheet 4 and the backsheet 5 and bonded under tension to at least one of these sheets 4, 5. The side edges 2c, 2c of the front waist region 2 defining the leg-openings 8, 8 are respectively provided with a plurality of elastic members 14 circumferentially extending to be associated with the respect leg-openings 8, 8. These elastic members 14, 14 are disposed between the topsheet 4 and the backsheet 5 and bonded under tension to at least one of the topsheet 4 and the backsheet 5.

The topsheet 4 defining the inner surface of the front waist region 2 is formed with a first lower fastening zone 9 transversely extending in the vicinity of the lower end 2b of the front waist region 2 and a first upper fastening zone 10 transversely extending and spaced apart from the first lower fastening zone 9 toward the upper end 2a by a desired dimension.

The rear waist region 3 comprises a liquid-pervious topsheet 4 defining the inner surface of the rear waist region 3, a liquid-impervious backsheet 5 defining the outer surface of the rear waist region 3 and a liquid-absorbent core 6 disposed between these topsheet 4 and backsheet 5. The topsheet 4 and the backsheet 5 are put flat and bonded together along their peripheral edges. The core 6 is bonded to at least one of the topsheet 4 and the backsheet 5.

The rear waist region 3 is provided along its upper end 3a with a film-like elastic member 15 extending circumferentially of the waist-opening 7. This elastic member 15 is disposed between the topsheet 4 and the backsheet 5 and bonded under tension to at least one of these sheets 4, 5. In the rear waist region 3, along the respective sections of its side edges 3c, 3c defining the respective leg-openings 8, 8 a plurality of elastic members 16 extend circumferentially of these leg-openings 8, 8. These elastic members 16 are disposed between the topsheet 4 and the backsheet 5 and bonded under tension to at least one of these sheets 4, 5.

The topsheet 4 defining the inner surface of the rear waist region 3 is formed with a second fastening zone 11 transversely extending in the vicinity of the lower end 3b of the rear waist region 3. The backsheet 5 defining the outer surface of the rear waist region 3 is formed with a third fastening zone 12 transversely extending and spaced apart from the second fastening zone 11 toward the upper end 3a by a desired dimension. Referring to FIG. 1, the second fastening zone 11 of the rear waist region 3 is releasably engaged with the first upper fastening zone 10 of the front waist region 2 while the third fastening zone 12 of the rear waist zone 3 is releasably engaged with the first fastening zone 9 of the front waist region 2.

As will be best seen in FIG. 2, the inner surface of the front waist region 2 is fastened with the inner surface of the rear waist region 3 along the first upper fastening zone 10 and the second fastening zone 11, and along the first lower fastening zone 9 and the third fastening zone 12.

The lower end 2b of the front waist region 2 lies on the outer surface of the rear waist region 3. The lower end 3b of the rear waist region 3 extend across the wearer's crotch toward the wearer's belly and is partially folded onto the outer surface of the diaper 1. In this way, it is ensured that the lower end 3b is kept out of contact with the wearer's skin during use of the diaper 1.

The locations of the front and rear waist regions 2, 3 at which the first lower fastening zone 9, first upper fastening zone 10 and second fastening zone 11 are provided are free from the presence of the core 6 disposed between the topsheet 4 and the backsheet 5. This arrangement is effective to avoid a problem that the diaper 1 might become bulky in those fastening zones 9, 10, 11, 12 even when they are engaged one with another to put the diaper 1 on the wearer's body.

With this diaper 1, the fastening zones 9, 10, 11, 12 are covered with the front waist region 2 and not exposed on the outer side of the diaper 1 after the front and rear waist regions 2, 3 are temporarily connected to each other along these fastening zones 9, 10, 11, 12 and therefore the appearance of the diaper 1 is never affected by these fastening zones. In addition, the core 6 extend from the rear waist region 3 across the wearer's crotch into the wearer's belly side so that urine discharged on the side of the front waist region 2 can be reliably absorbed by the core 6 without any apprehension of urine leakage.

Figure 3:
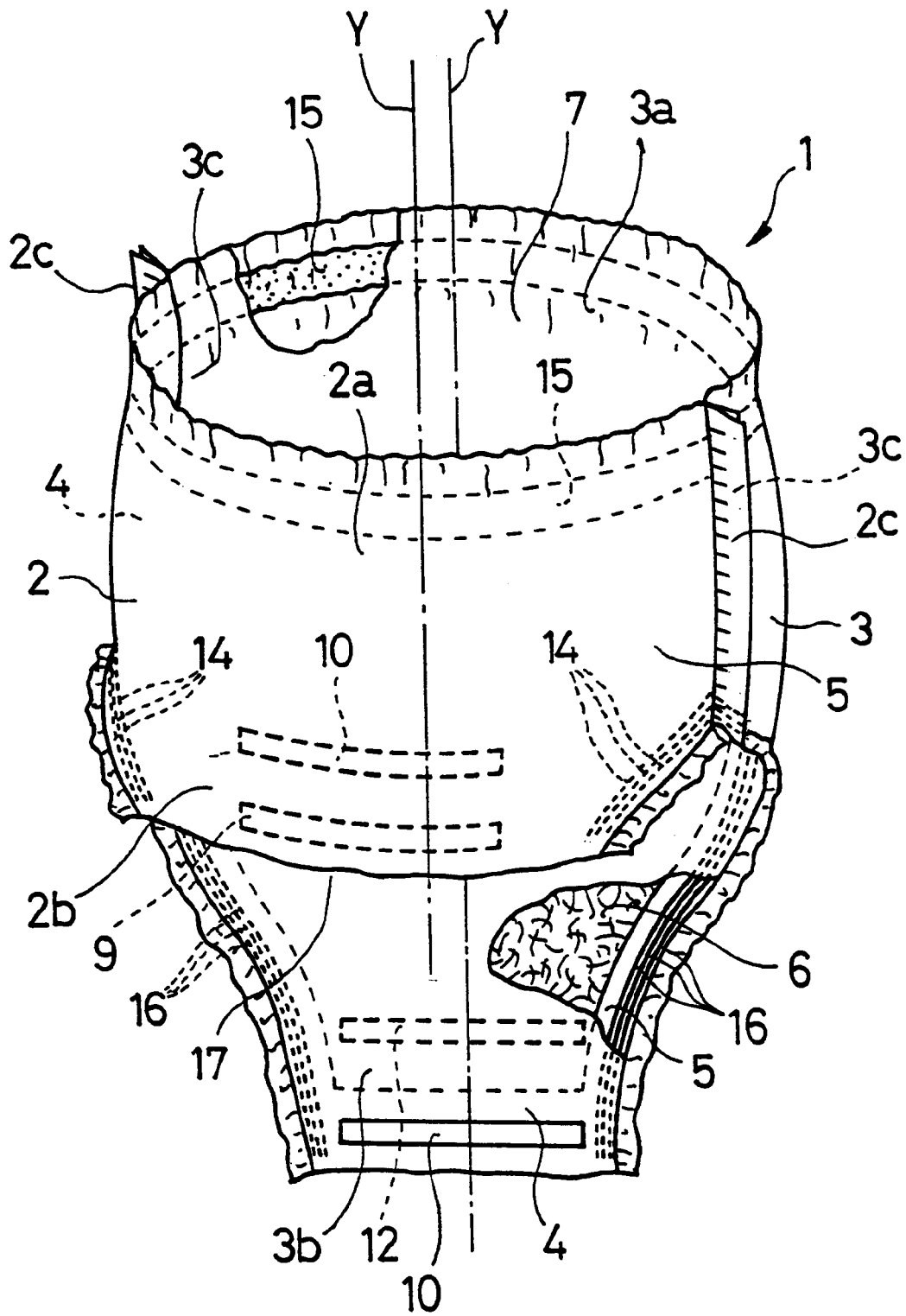
FIG. 3 is a perspective view illustrating a first step of wearing the diaper.
Figure 4:
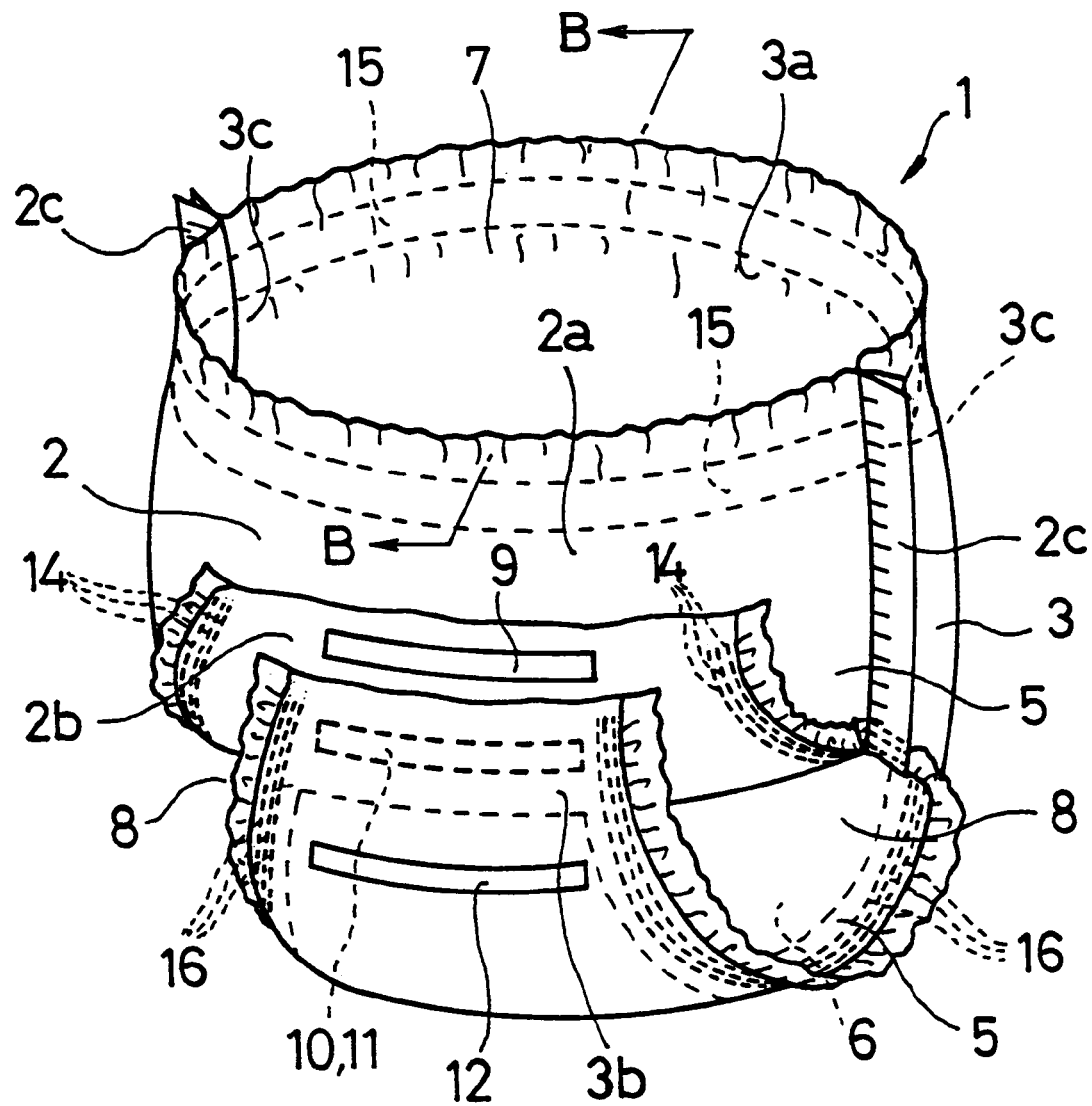
FIG. 4 is a view similar to FIG. 3 illustrating a second step of wearing the diaper.
Figure 5:
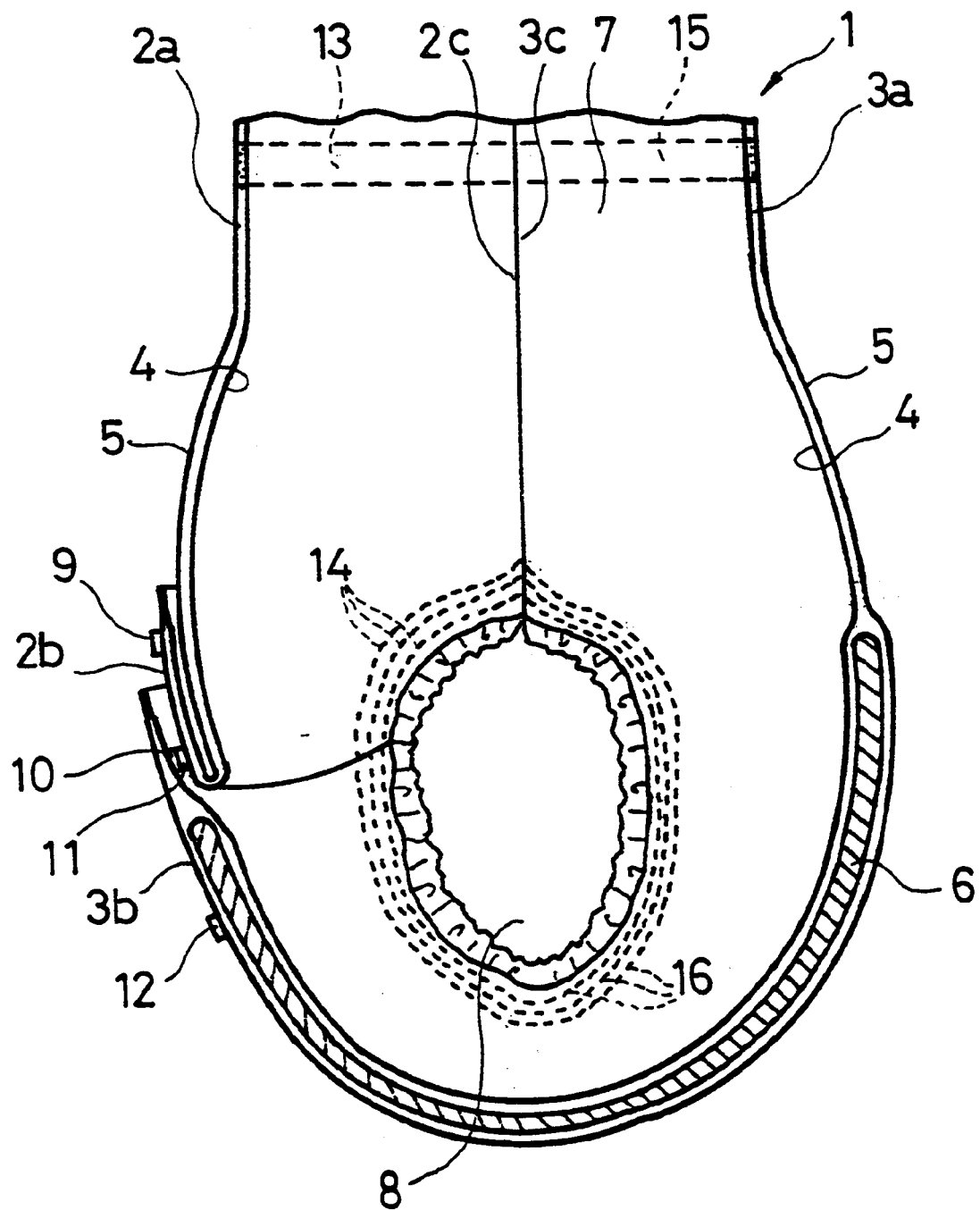
FIG. 5 is a sectional view taken along line B—B in FIG. 4.

FIGS. 3 and 4 are perspective view illustrating a step of wearing the diaper and FIG. 5 is a sectional view taken along line B—B in FIG. 4. The first lower fastening zone 9 of the front waist region 2 is disengaged from the third fastening zone 12 of the rear waist region 3 and the first upper fastening zone 10 of the front waist region 2 is disengaged from the second fastening zone 11 of the rear waist region 3 to form a lower opening 17 through which the wearer's legs can pass, as illustrated in FIG. 3. From the state illustrated by FIG. 3, the diaper 1 is pulled upward first around the waist-opening 7 and then around the lower opening 17 until the waist-opening 7 of the diaper 1 reaches the wearer's waist line. Now, along the first upper fastening zone 10 and the second fastening zone 11 the inner surface of the front waist region 2 is engaged with the inner surface of the rear waist region 3 to establish a state shown in FIG. 5. Finally, the inner surface of the front waist region 2 is engaged with the outer surface of the rear waist region 3 to establish the state shown in FIG. 1.

With this diaper 1, the respective lower ends 2b, 3b of the front and rear waist regions 2, 3 are releasably fastened together along the fastening zones 9, 10, 11, 12 provided on the respective waist regions 2, 3. Such arrangement allows the diaper 1 to be put on the wearer's body without any need for completely pulling off wearer's clothes such as trousers or tights, even if such clothes are already put on the wearer's body. In other words, the clothes may be pull down to the level of the wearer's knees immediately before putting the diaper 1 on the wearer's body.

Preferably, the first lower fastening zone 9 and the first upper fastening zone 10 of the front waist region 2 may be one of a tape fastener made of a flexible plastic material coated with a pressure-sensitive adhesive to define a adhesive area and a target tape strip made of a flexible plastic material on which an adhesive area of a tape fastener can be temporarily anchored while the second fastening zone 11 and the third fastening zone 12 of the rear waist region 3 may be the other of the tape fastener and the target tape strip. Alternatively, the first lower fastening zone 9 and the first upper fastening zone 10 of the front waist region 2 may be one of a hook member and a loop member constituting together a mechanical fastener while the second fastening zone 11 and the third fastening zone 12 of the rear waist region 3 may be the other of the hook member and the loop member.

The front and rear waist regions 2, 3, at least the rear waist region 3, may further include a pair of leak-barrier cuffs longitudinally extending along the transversely opposite side edges 2c, 2c; 3c, 3c thereof. In the case of the diaper 1 provided with such pair of leak-barrier cuffs, these cuffs can almost entirely surround the wearer's thighs and reliably prevent sideways leakage of excretion since the rear waist region 3 extends across the wearer's crotch to the side of the wearer's belly.

In the front waist region 2 of the diaper 1, it is also possible to provide an additional fastening zone of a given dimension so that this additional fastening zone may extend from the vicinity of the lower end 2b toward the upper end 2a when the first lower fastening zone 9 is engaged with the first upper fastening zone 10.

It is possible without departing from the scope and the spirit of this invention to provide the front waist region 2 also with the liquid-absorbent core 6 disposed between the liquid-pervious topsheet 4 and the liquid-impervious backsheet 5. It is also possible to configure the front and rear waist regions 2, 3 to have the same dimension between the longitudinally opposite ends 2a, 2b; 3a, 3b thereof, respectively.

The topsheet 4 may be formed with a liquid-pervious sheet such as a nonwoven fabric or porous plastic film, preferably by a liquid-pervious hydrophilic sheet. The backsheet 5 may be formed with a hydrophobic nonwoven fabric, a liquid-impervious plastic film or a laminated sheet composed of a hydrophobic nonwoven fabric and a plastic film, preferably by a breathable but liquid-impervious sheet. It is also possible to use, as a stock material for the backsheet 5, composite a nonwoven fabric (SMS nonwoven fabric) comprising a melt blown nonwoven fabric having a high water-resistance, of which the opposite sheet surfaces are sandwiched between sheet surfaces of the melt blown nonwoven fabric having a high strength and a high flexibility.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. The component fiber of the nonwoven fabric may be selected from a group including polyolefine, polyester and polyamide fibers and conjugated fiber of polyethylene/polypropylene or polyester.

The core 6 may be formed with a mixture of fluff pulp and high absorption polymer particles compressed to a desired thickness. Bonding or attachment of the core 6, the sheets 4, 5 and the elastic members 13, 14, 15, 16 may be carried out using a suitable adhesive such as a hot melt adhesive or a pressure-sensitive adhesive or a heat-sealing technique.

This invention is applicable not only to the disposable diaper 1 but also to a diaper cover. In the case of the diaper cover, an absorbent inner pad may be bonded to the inner surface of front or rear waist region of such cover and the steps illustrated by FIGS. 3 and 4 may be followed to put the cover on the wearer's body.

What is claimed is:

1. A disposable pull-on undergarment comprising:

a front waist region having longitudinally opposite upper and lower ends and transversely opposite side edges;

a rear waist region having longitudinally opposite upper and tower ends and transversely opposite side edges with sections of said side edges thereof extending aside from said upper ends being bonded to sections of said side edges of said rear waist region which extend aside from said upper ends of said rear waist regions to form a waist-opening, said rear waist region further including a liquid-pervious topsheet defining an inner surface thereof and a liquid-impervious backsheet defining an outer surface thereof;

a liquid-absorbent core disposed between said liquid-pervious topsheet and said liquid-impervious backsheet; and fastening zones provided on said lower ends of said front and rear waist regions along which said lower ends of said front and rear waist regions are releasably fastened together, said fastening zones including a first fastening zone provided on an inner surface of said front waist region and extending from a vicinity of said lower end toward said upper end of said front waist region, a second fastening zone provided on an inner surface of the rear waist region in vicinity of said lower end and releasably engaged with said first fastening zone lying adjacent said upper end of said front waist region and a third fastening zone provided on an outer surface of said rear waist region and spaced apart from said second fastening zone toward said upper end so that said third fastening zone is engaged with said first fastening zone lying adjacent said lower end of said front waist region, said first, second and third fastening zones each having a width and a length which is greater than the width, the length of each of the first, second and third fastening zones extending in a transverse direction of the undergarment and being parallel to one another along the transverse direction.

2. The undergarment according to claim 1, wherein a longitudinal dimension of said front waist region as measured between the upper and lower ends thereof is smaller than that of said rear waist region and said front and rear waist regions have the lower ends thereof that are releasably fastened together at a location lying aside to said wearer's belly along said fastening zones.

3. A disposable pull-up undergarment comprising:

a front waist region having longitudinally opposite upper and lower ends and transversely opposite side edges;

a rear waist region having longitudinally opposite upper and lower ends and transversely opposite side edges with sections of said side edges thereof extending aside from said upper ends being bonded to sections of said side edges of said rear waist region which extend aside from said upper ends of said rear waist regions to form a waist-opening, said rear waist region further including a liquid-absorbent core; and fastening zones provided on said lower ends of said front and rear waist regions along which said lower ends of said front and rear waist regions are releasably fastened together, said fastening zones including a first fastening zone provided on an inner surface of said front waist region and extending from a vicinity of said lower end toward said upper end of said front waist region, a second fastening zone provided on the inner surface in vicinity of said lower end and releasably engaged with said first fastening zone lying adjacent said upper end of said front waist region and a third fastening zone provided on an outer surface of said rear waist region and spaced apart from said second fastening zone toward said upper end so that said third fastening zone is engaged with said first fastening zone lying adjacent said lower end of said front waist region, said first, second and third fastening zones each having a width and a length which is greater than the width, the length of each of the first, second and third fastening zones extending in a transverse direction of the undergarment and being parallel to one another along the transverse direction, wherein said first fastening zone comprises a first lower fastening zone lying in the vicinity of said lower end of said front waist region and a first upper fastening zone spaced apart from said first lower fastening zone toward said upper end so that said second fastening zone is releasably engaged with said first upper fastening zone and said third fastening zone is releasably engaged with said first lower fastening zone.

4. The undergarment according to claim 3, wherein a longitudinal dimension of said front waist region as measured between the upper and lower ends thereof is smaller than that of said rear waist region and said front and rear waist regions have the lower ends thereof that are releasably fastened together at a location lying aside to said wearer's belly along said fastening zones.

5. A disposable pull-on undergarment comprising:
   a front waist region having longitudinally opposite upper and lower ends and transversely opposite side edges;
   a rear waist region having longitudinally opposite upper and lower ends and transversely opposite side edges with sections of said side edges thereof extending aside from said upper ends being bonded to sections of said side edges of said rear waist region which extend aside from said upper ends of said rear waist regions to form a waist-opening, said rear waist region further including
      a liquid-pervious topsheet defining an inner surface thereof and a liquid-impervious backsheet defining an outer surface thereof;
      a liquid-absorbent core disposed between said liquid-pervious topsheet and said liquid-impervious backsheet; and
   fastening zones provided on said lower ends of said front and rear waist regions along which said lower ends of said front and rear waist regions are releasably fastened together,
   said fastening zones including a first fastening zone provided on an inner surface of said front waist region and extending from a vicinity of said lower end toward said upper end of said front waist region, a second fastening zone provided on an inner surface of the rear waist region in vicinity of said lower end and releasably engaged with said first fastening zone lying adjacent said upper end of said front waist region and a third fastening zone provided on an outer surface of said rear waist region and spaced apart from said second fastening zone toward said upper end so that said third fastening zone is engaged with said first fastening zone lying adjacent said lower end of said front waist region, said first, second and third fastening zones each having a width and a length which is greater than the width, the length of each of the first, second and third fastening zones extending in a transverse direction of the undergarment and being parallel to one another along the transverse direction, said second and third fastening zones engage the first fastening zone between an area where the front waist region overlaps the rear waist region.

6. The undergarment according to claim 5, wherein a longitudinal dimension of said front waist region as measured between the upper and lower ends thereof is smaller than that of said rear waist region and said front and rear waist regions have the lower ends thereof that are releasable fastened together at a location lying aside to said wearer's belly along said fastening zones.

7. A disposable pull-up undergarment comprising:
   a front waist region having longitudinally opposite upper and lower ends and transversely opposite side edges;
   a rear waist region having longitudinally opposite upper and lower ends and transversely opposite side edges with sections of said side edges thereof extending aside from said upper ends being bonded to sections of said side edges of said rear waist region which extend aside from said upper ends of said rear waist regions to form a waist-opening, said rear waist region further including a liquid-absorbent core; and
   fastening zones provided on said lower ends of said front and rear waist regions along which said lower ends of said front and rear waist regions are releasably fastened together,
   said fastening zones including a first fastening zone provided on an inner surface of said front waist region and extending from a vicinity of paid lower end toward said upper end of said front waist region, a second fastening zone provided on the inner surface in vicinity of said lower end and releasably engaged with said first fastening zone lying adjacent said upper end of said front waist region and a third fastening zone provided on an outer surface of said rear waist region and spaced apart from said second fastening zone toward said upper end so that said third fastening zone is engaged with said first fastening zone lying adjacent said lower end of said front waist region, said first, second and third fastening zones each having a width and a length which is greater than the width, the length of each of the first, second and third fastening zones extending in a transverse direction of the undergarment and being parallel to one another along the transverse direction, wherein said first fastening zone comprises a first lower fastening zone laying in the vicinity of said lower end of said front waist region and a first upper fastening zone spaced apart from said first lower fastening zone toward said upper end so that said second fastening zone is releasably engaged with said first upper fastening zone and said third fastening zone if releasably engaged with said first lower fastening zone.

8. The undergarment according to claim 7, wherein a longitudinal dimension of said front waist region as measured between the upper and lower ends thereof is smaller than that of said rear waist region and said front and rear waist regions have the lower ends thereof that are releasable fastened together at a location lying aside to said wearer's belly along said fastening zones.

* * * * *